United States Patent
Delgado et al.

(10) Patent No.: US 7,799,930 B2
(45) Date of Patent: Sep. 21, 2010

(54) 1-ALKYL-3-AMINOINDAZOLES

(75) Inventors: Pete Delgado, Fort Worth, TX (US); Raymond E. Conrow, Crowley, TX (US); W. Dennis Dean, Burleson, TX (US)

(73) Assignee: Alcon, Inc., Hunenberg (CH)

( * ) Notice: Subject to any disclaimer, the term of this patent is extended or adjusted under 35 U.S.C. 154(b) by 0 days.

(21) Appl. No.: 12/368,869

(22) Filed: Feb. 10, 2009

(65) Prior Publication Data

US 2009/0149659 A1    Jun. 11, 2009

Related U.S. Application Data

(62) Division of application No. 10/539,423, filed as application No. PCT/US03/40370 on Dec. 19, 2003, now abandoned.

(60) Provisional application No. 60/436,385, filed on Dec. 23, 2002.

(51) Int. Cl.
    *C07D 231/56* (2006.01)
(52) U.S. Cl. .................................. 548/362.1
(58) Field of Classification Search ............... 548/362.1
    See application file for complete search history.

(56) References Cited

U.S. PATENT DOCUMENTS

| 3,133,081 | A |   | 5/1964  | Laffery et al. |           |
|-----------|---|---|---------|----------------|-----------|
| 3,681,382 | A |   | 8/1972  | Gschwend       |           |
| 3,711,506 | A | * | 1/1973  | Wagner et al.  | 548/362.1 |
| 3,725,431 | A |   | 4/1973  | Gschwend       |           |
| 3,963,739 | A |   | 6/1976  | Steffen        |           |

FOREIGN PATENT DOCUMENTS

| WO | WO9830548 A1  | 7/1998  |
| WO | WO02098861 A1 | 12/2002 |
| WO | WO02098862 A1 | 12/2002 |

OTHER PUBLICATIONS

Applegate, et al., The Efficient Synthesis of 3-Arlysydnones Under Neutral Conditions, Synthesis, 1988, pp. 1011-1012.
Brown, et al., 1,3,6-Trisubstituted Indoles as Peptidoleukotriene Antagonists: Benefits of a Second, Polar, Pyrrole Substituent, J. Med. Chem., 1992, pp. 2419-2439, vol. 35.
Caron, et al., A Versatile and Efficient Synthesis of Substituted 1H-Indazoles, Synthesis, 1999, pp. 588-592, vol. 4.
Fieser, et al., Nickel catalysts (a), Raney type, Reagents for Organic Synthesis, 1967, pp. 723-731, vol. 1.
Finch, et al., Rearrangement of 3-Amino-l-benzylindazole to 4-Amino-2-phenylquinazoline, J. Org. Chem., 1971, pp. 1463-1465, vol. 36(11).
Fischer, et al., ueber die Hydrazine der Zimmtsaure, Justus Liebigs Annalen der Chemie, 1884, pp. 302-341, vol. 227.
Halley, et al., Synthesis of 5-Cyanoindazole and 1-Methyl and 1-Aryl-5-Cyanoindazoles, Synthetic Communications, 1997, pp. 1199-1207, vol. 27(7).
Kawakubo, et al., Studies on 3-Aminoindazoles. I. Synthesis of 1- or 3-(Substituted 3-Amino)indazoles, Chem. Pharm. Bull., 1987, pp. 2292-2299, vol. 35(6).
Lark, et al., A Potent Small Molecule, Nonpeptide Inhibitor of Cathepsin K (SB 331750) Prevents Bone Matrix Resorption in the Ovariectomized Rat, Bone, 2002, pp. 746-753, vol. 30(5).
Leung-Toung, et al., Thiol-Dependent Enzymes and Their Inhibitors: A Review, Current Medicinal Chemistry, 2002, pp. 979-1002, vol. 9.
McGeachin, et al., The Structures of Two Self-Condensation Products from o-Aminobenzaldehyde, Canadian J. of Chemistry, 1966, pp. 2323-2328, vol. 4.
March, Reactions, Mechanisms, and Structure, Advanced Organic Chemistry, 4th Edition, John Wiley and Sons, New York, pp. 721-723, 1992.
Matassa, et al., Evolution of a Series of Peptidoleukotriene Antagonists: Synthesis and Structure/Activity Relationships of 1,3,5-Substituted Indoles and Indazoles, J. Med. Chem., 1990, pp. 1781-1790, vol. 33.
Parnell, et al., 2-Cyano-4-nitrophenylhydrazine and 3-Amino-5-nitroindazoles, J. Chem. Soc., 1959, pp. 2363-2365.
Patil, et al., A New Dimeric Dihydrochalcone and a New Prenylated Flavone from the Bud Covers of *Artocarpus altilis*: Potent Inhibitors of Cathepsin K, J. Nat. Prod., 2002, pp. 624-627, vol. 65.
Patil, et al., Haploscleridamine, a Novel Tryptamine-Derived Alkaloid from a Sponge of the Order Haplosclerida: An Inhibitor of Cathepsin K, J. Nat. Prod., 2002, pp. 628-629, vol. 65.
Pontikis, et al., A New Route to 2'-C-methylene Nucleoside Analogs, Inhibitors of Ribonucleotide Reductase, Tetrahedron Letters, 1995, pp. 3523-3526, vol. 36(20).
Smith, et al., Discovery and Parallel Synthesis of a New Class of Cathepsin K Inhibitors, Bioorganic & Medicinal Chemistry Letters, 2001, pp. 2951-2954, vol. 11.
Song, et al., A Novel Synthesis of 2-Aryl-2H-indazoles via a Palladium-Catalyzed Intramolecular Amination Reaction, 2000, pp. 519-521, vol. 2(4)I.
Stroup, et al., Potent and Selective Inhibition of Human Cathepsin K Leads to Inhibition of Bone Resorption In Vivo in a Nonhuman Primate, J. of Bone and Mineral Research, 2001, pp. 1739-1746, vol. 16(10).
Suwinski, et al., The Mechanism of Elimination of Aldoxime Hydrogensulfates to Nitriles, Polish J. of Chemistryl, 1985, pp. 521-529, vol. 59.

(Continued)

*Primary Examiner*—Rebecca L Anderson
*Assistant Examiner*—Shawquia Young
(74) *Attorney, Agent, or Firm*—Patrick M. Ryan

(57) ABSTRACT

Methods of making 1-alkylindazoles are described. The methods involve reacting a 2-alkylaminobenzonitrile with a nitrosating agent followed by reduction-cyclization of the resulting nitrosamine to form a 1-alkyl-3-aminoindazole. The 1-alkyl-3-aminoindazole can be deaminated to form a 1-alkylindazole which ultimately can be used to form desired indazoles which are preferably pharmaceutically active products. The process of the present invention further permits the formation of enantiomerically enriched or pure indazoles such as aminoalkyl indazoles.

2 Claims, No Drawings

OTHER PUBLICATIONS

Vivona, et al., Mononuclear Heterocyclic Rearrangements. Part 12(1). Rearrangements of 1,2,4-Oxadiazoles into Indazoles, J. of Heterocyclic Chemistry, 1979, pp. 783-784, vol. 16(1).

Von Auwers, et al., Uber Synthesen von N-Acyl-indzolen, Justus Liebigs Annalen der Chemie, 1926, pp. 273-303, vol. 450.

Bamberger, Eugen, Action of alkalis on orthomethyldiazonium salts, Justus Liebigs Annalen der Chemie, 1899, pp. 314-331, vol. 305.

Akazome, et al., Palladium Complex-Catalyzed Reductive N-Heterocyclization of Nitroarenes: Novel Synthesis of Inddole and 2H-Indazole Derivatives, J. of Org. Chem, 1994, pp. 3375-3380, vol. 59.

Al-Khamees, et al., Synthesis of (±)-(4aS, 13cR)- and (±)-(4aR, 13cR)-1,2,3,4,4a,13c-Hexahydro-5H-indazolo[2,3-d][1,4]benzodiazepin-6(7H)-ones, J. Chem. Soc., Perkin Trans 1, 1985, pp. 2001-2006.

Altmann, et al., Arylaminoethyl Amides as Novel Non-Covalent Cathepsin K Inhibitors, J. Med. Chem., 2002, pp. 2352-2354, vol. 45.

* cited by examiner

1-ALKYL-3-AMINOINDAZOLES

This application is a divisional of U.S. Ser. No. 10/539,423, filed Jun. 20, 2005, which is a 371 application of PCT/US03/40370, filed Dec. 19, 2003, which claims the benefit of U.S. Provisional Application, Ser. No. 60/436,385, filed Dec. 23, 2002.

BACKGROUND OF THE INVENTION

1. Field of the Invention

The present invention relates to 1-alkyl-3-aminoindazoles and preferably 1-(hydroxyalkyl)-3-aminoindazoles useful as intermediates for the preparation of 1-alkylindazoles. Use of the 1-alkyl-3-aminoindazoles as intermediates avoids unwanted side products and results in enantiomerically pure final pharmaceutically active products.

2. Description of the Related Art

Certain (aminoalkyl)indazoles are known to be useful for treating diseases of the central nervous system (WO 98/30548). WO 02/098861 A1 and WO 02/098862 A1 disclose methods of preparation of (aminoalkyl)indazoles. Specifically, these applications disclose the conversion of 2-(hydroxyalkyl)aminobenzaldehydes to 1-(hydroxyalkyl)indazoles, which are useful intermediates for the preparation of 1-(aminoalkyl)indazoles.

The following references generally describe 1-alkyl-3-aminoindazoles: U.S. Pat. Nos. 3,725,431, 3,681,382, 3,133,081; DE 2,248,175; Kawakubo et al. (1987); Vivona et al. (1979); Bouchet et al. (1980), Parnell (1959). Notably, Finch and Gschwend (1971) teach that nitrosation of 2-benzylaminobenzonitrile (N-benzylanthranilonitrile) followed by reduction produces the uncyclized hydrazino benzonitrile.

There is a need to provide further processes and intermediates to manufacture 1-(aminoalkyl)indazoles which avoid undesired isomers and which are capable of producing large quantities of the desired compound.

All patents, patent applications, and publications referenced in this application are incorporated in their entirety and form a part of the present application.

SUMMARY OF THE PRESENT INVENTION

The present invention overcomes the above mentioned problems and other drawbacks of the prior art by providing a method, capable of scaleup, to efficiently produce large quantities of 1-(aminoalkyl)indazoles. More specifically, the present invention provides a method of making 1-(aminoalkyl)indazoles in large quantities while avoiding large quantities of undesired isomers or by-products.

To achieve these and other advantages and in accordance with the purposes of the present invention, as embodied and properly described herein, the present invention relates to a method of making a 1-alkylindazole involving:

a) the nitrosation and reduction-cyclization of a 2-alkylaminobenzonitrile to form a 1-alkyl-3-aminoindazole; and b) deamination of the 1-alkyl-3-aminoindazole to form a 1-alkylindazole.

In a preferred embodiment, the present invention relates to a method of making a is 1-(hydroxyalkyl)indazole involving:

a) the nitrosation and reduction-cyclization of a 2-hydroxyalkyl)aminobenzonitrile to form a 1-(hydroxyalkyl)-3-aminoindazole; and b) deamination of the 1-(hydroxyalkyl)-3-aminoindazole to form a 1-(hydroxyalkyl)indazole.

Additional features and advantages of the present invention will be set forth in part in the description that follows, or may be learned by practice of the present invention. The objectives and other advantages of the present invention will be realized and attained by means of the elements and combinations particularly pointed out in the description and appended claims. It is to be understood that both the foregoing general description and the following detailed description are exemplary and explanatory only and are intended to provide a further explanation of the present invention, as claimed.

DETAILED DESCRIPTION OF THE PRESENT INVENTION

The present invention relates to 1-alkyl-3-aminoindazoles. More particularly, the present invention relates to the use of 1-alkyl-3-aminoindazoles as intermediates for making 1-alkylindazoles. A preferred embodiment of the present invention relates to 1-(hydroxyalkyl)-3-aminoindazoles, and particularly to the use of 1-(hydroxyalkyl)-3-aminoindazoles for making 1-(aminoalkyl)indazoles. The 1-(aminoalkyl)indazoles that can be made following the methods of the present invention are preferably enantiomerically pure products which are preferably useful as pharmacologically active products such as in the treatment of glaucoma and/or are useful for lowering and controlling normal or elevated intraocular pressure. The methods described herein avoid the problems associated with removal of acetic acid and are capable of scaleup to produce large quantities of material for formulation in pharmaceutical compositions.

In previous processes for producing 1-(hydroxyalkyl)indazoles, such as those set forth in WO 02/098862 A1 and WO 02/098861 A1, the reaction proceeds via nitrosation of a 2-(hydroxyalkyl)aminobenzaldehyde followed by reduction-cyclization to form the 1-(hydroxyalkyl)indazole. These steps utilized as a preferred solvent acetic acid, which is difficult to remove, as the solvent, and the by-products were difficult to remove. The process of the present invention, on the other hand, uses readily removed solvents and produces readily removed by-products.

In the methods of the present invention, 1-alkylindazoles can be produced by 1 nitrosating a 2-alkylaminobenzonitrile, followed by reduction and cyclization, to form a 1-alkyl-3-aminoindazole. This aminoindazole can then be deaminated to form a 1-alkylindazole. Preferred among the 1-alkylindazoles that may be prepared according to the methods of the present invention are those of the formula:

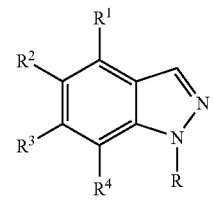

wherein R is a $C_2$ to $C_{12}$ (hydroxy)alkyl group optionally substituted with phenyl, methoxyphenyl, (dimethylamino)phenyl, $OR^5$, $OC(=O)R^5$, $OC(=O)OR^5$, $N(R^5)_2$, $N(R^5)C(=O)R^5$, $N(R^5)C(=O)OR^5$, or with one or more F atoms;

$R^1$, $R^2$, $R^3$ and $R^4$ are independently H, F, Cl, Br, $CF_3$, OH, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $N_3$, SH, $S(O)_nR^5$, $C(=O)R^5$, COOH, COOR$^5$, CON(R$^5$)$_2$, C$_1$ to C$_6$ alkyl optionally substituted with phenyl, methoxyphenyl, (dimethylamino)phenyl, C(=O)R$^5$, COOH, COOR$^5$, CON(R$^5$)$_2$, CN, OR$^5$, OC(=O)R$^5$, OC(=O)OR$^5$, N(R$^5$)$_2$, N(R$^5$)C(=O)R$^5$, or N(R$^5$)C(=O)OR$^5$; or R$^1$ and R$^2$ as herein defined taken together form a ring, or R$^2$ and R$^3$ as herein defined taken together form a ring, or R$^3$ and R$^4$ as herein defined taken together form a ring;

R$^5$ is C$_1$ to C$_6$ alkyl optionally substituted with phenyl, methoxyphenyl, (dimethylamino)phenyl, methoxy, ethoxy, benzyloxy, or with one or more F atoms, or R$^5$ is phenyl, methoxyphenyl, or (dimethylamino)phenyl; and n=0, 1, or 2.

Most preferred among the 1-alkylindazoles of the foregoing formula are those wherein R is a C$_2$ to C$_6$ (hydroxy)alkyl optionally substituted with phenyl, OR$^5$, N(R$^5$)C(=O)R$^5$, N(R$^5$)C(=O)OR$^5$, or with one or more F atoms;

R$^1$, R$^2$, R$^3$ and R$^4$ are independently H, F, Cl, CF$_3$, OR$^5$, OC(=O)R$^5$, OC(=O)OR$^5$, N(R$^5$)$_2$, N(R$^5$)C(=O)R$^5$, N(R$^5$)C(=O)OR$^5$, NO$_2$, CN, C(=O)R$^5$, COOR$^5$, CON(R$^5$)$_2$, C$_1$ to C$_6$ alkyl optionally substituted with phenyl, C(=O)R$^5$, COOR$^5$, CON(R$^5$)$_2$, CN, OR$^5$, OC(=O)R$^5$, OC(=O)OR$^5$, N(R$^5$)$_2$, N(R$^5$)C(=O)R$^5$, or N(R$^5$)C(=O)OR$^5$; or R$^1$ and R$^2$ as herein defined taken together form a ring, or R$^2$ and R$^3$ as herein defined taken together form a ring, or R$^3$ and R$^4$ as herein defined taken together form a ring;

R$^5$ is C$_1$ to C$_6$ alkyl optionally substituted with phenyl, methoxyphenyl, methoxy, benzyloxy, or with one or more F atoms.

In a preferred embodiment of the present invention, the nitrosation can be carried out on a 2-(hydroxyalkyl)aminobenzonitrile, followed by reduction and cyclization, to form a 1-(hydroxyalkyl)-3-aminoindazole. This 1-(hydroxyalkyl)-3-aminoindazole can then be deaminated to form a 1-(hydroxyalkyl)indazole.

Preferably, the steps of nitrosation/reduction-cyclization and deamination are carried out using a readily removable solvent. Preferred solvents for use in the methods of the present invention include tetrahydrofuran and methanol. This 1-(hydroxyalkyl)indazole can then be further reacted to form a desired 1-(aminoalkyl)indazole which is preferably enantiomerically pure and is preferably a pharmaceutically active product. The 1-(hydroxyalkyl)indazole can be reacted with a sulfonyl halide or sulfonic anhydride to form a corresponding sulfonic ester. This sulfonic ester can be reacted with a metal azide to yield a 1-(azidoalkyl)indazole which in turn is reacted with a hydrogen source and a catalyst to yield a 1-(aminoalkyl)indazole. The hydrogen source is preferably ammonium formate and the catalyst is preferably palladium on charcoal in the presence of an organic solvent, such as ethanol.

Preferably, the 2-(hydroxyalkyl)aminobenzonitrile has the formula

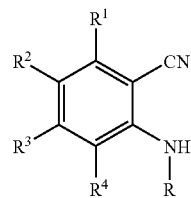

In this formula, R is a C$_2$ to C$_{12}$ alkyl group substituted with at least one OH group and optionally substituted with phenyl, methoxyphenyl, (dimethylamino)phenyl, OR$^5$, OC(=O)R$^5$, OC(=O)OR$^5$, N(R$^5$)$_2$, N(R$^5$)C(=O)R$^5$, N(R$^5$)C(=O)OR$^5$, or with one or more F atoms; R$^1$, R$^2$, R$^3$ and R$^4$ are independently H, F, Cl, Br, CF$_3$, OH, OR$^5$, OC(=O)R$^5$, OC(=O)OR$^5$, N(R$^5$)$_2$, N(R$^5$)C(=O)R$^5$, N(R$^5$)C(=O)OR$^5$, NO$_2$, CN, N$_3$, SH, S(O)$_n$R$^5$, C(=O)R$^5$, COOH, COOR$^5$, CON(R$^5$)$_2$, C$_1$ to C$_6$ alkyl optionally substituted with phenyl, methoxyphenyl, (dimethylamino)phenyl, C(=O)R$^5$, COOH, COOR$^5$, CON(R$^5$)$_2$, CN, OR$^5$, OC(=O)R$^5$, OC(=O)OR$^5$, N(R$^5$)$_2$, N(R$^5$)C(=O)R$^5$, or N(R$^5$)C(=O)OR$^5$; or R$^1$ and R$^2$ as herein defined taken together form a ring, or R$^2$ and R$^3$ as herein defined taken together form a ring, or R$^3$ and R$^4$ as herein defined taken together form a ring; R$^5$ is C$_1$ to C$_6$ alkyl optionally substituted with phenyl, methoxyphenyl, (dimethylamino)phenyl, methoxy, ethoxy, benzyloxy, or with one or more F atoms, or R$^5$ is phenyl, methoxyphenyl, or (dimethylamino)phenyl; and n=0, 1, or 2.

More preferably, R is a C$_2$ to C$_6$ alkyl group substituted with at least one OH group and optionally substituted with phenyl, OR$^5$, N(R$^5$)C(=O)R$^5$, N(R$^5$)C(=O)OR$^5$, or with one or more F atoms; R$^1$, R$^2$, R$^3$ and R$^4$ are independently H, F, Cl, CF$_3$, OR$^5$, OC(=O)R$^5$, OC(=O)OR$^5$, N(R$^5$)$_2$, N(R$^5$)C(=O)R$^5$, N(R$^5$)C(=O)OR$^5$, NO$_2$, CN, C(=O)R$^5$, COOR$^5$, CON(R$^5$)$_2$, C$_1$ to C$_6$ alkyl optionally substituted with phenyl, C(=O)R$^5$, COOR$^5$, CON(R$^5$)$_2$, CN, OR$^5$, OC(=O)R$^5$, OC(=O)OR$^5$, N(R$^5$)$_2$, N(R$^5$)C(=O)R$^5$, or N(R$^5$)C(=O)OR$^5$; or R$^1$ and R$^2$ as herein defined taken together form a ring, or R$^2$ and R$^3$ as herein defined taken together form a ring, or R$^3$ and R$^4$ as herein defined taken together form a ring; R$^5$ is C$_1$ to C$_6$ alkyl optionally substituted with phenyl, methoxyphenyl, methoxy, benzyloxy, or with one or more F atoms, or R$^5$ is phenyl or methoxyphenyl.

The 2-alkylaminobenzonitrile which is used in the methods of the present invention can be prepared by any number of reaction schemes. For instance, the 2-alkylaminobenzonitrile can be formed by reacting a 2-fluorobenzonitrile with an alkylamine in an organic solvent. In a preferred embodiment, the alkylamine is a hydroxyalkylamine and the product is a 2-(hydroxyalkyl)aminobenzonitrile. For instance, a 2-fluorobenzonitrile can be reacted with 1-amino-2-propanol in the presence of an organic solvent to yield the desired 2-(2-hydroxypropyl)aminobenzonitrile. Besides these reaction schemes, other reaction schemes can be used to form the desired starting 2-alkylaminobenzonitrile. Those skilled in the art, in view of the present invention, can form a variety of starting 2-alkylaminobenzonitriles for purposes of the present invention.

As shown in the details of the preferred embodiment and Scheme 1 set forth below, the nitrosation can be accomplished by the addition of at least one organic nitrite or inorganic nitrite preferably in the presence of at least one organic solvent. Examples of suitable nitrites include, but are not limited to, tert-butyl nitrite, isobutyl nitrite, isoamyl nitrite or sodium nitrite. Preferred solvents include, but are not limited to, ethers, and a more preferred solvent is tetrahydrofuran. Combinations or mixtures of two or more nitrites can be used. This would also be true with respect to the other reactants in that combinations or mixtures of various reactants can be used. The intermediate nitrosamine is treated with a reducing agent in the presence of an organic solvent to effect reduction with concurrent cyclization, affording a preferred 1-(hydroxyalkyl)-3-aminoindazole. Preferably the reduction-cyclization step is conducted without isolation of the intermediate nitrosamine. Preferably the reducing agent is zinc, and the reduction is carried out in the presence of an acidic salt such as ammonium acetate or ammonium chloride. Preferably the organic solvent is tetrahydrofuran or methanol, or a mixture of tetrahydrofuran and methanol.

Included among the 1-(hydroxyalkyl)-3-aminoindazoles of the present invention are those of the following formula:

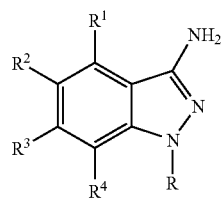

wherein R is a $C_2$ to $C_{12}$ (hydroxy)alkyl group optionally substituted with phenyl, methoxyphenyl, (dimethylamino)phenyl, $OR^5$, $OC(=O)R^5$, $OC(=O)OR^5$, $N(R^5)_2$, $N(R^5)C(=O)R^5$, $N(R^5)C(=O)OR^5$, or with one or more F atoms;

$R^1$, $R^2$, $R^3$ and $R^4$ are independently H, F, Cl, Br, $CF_3$, OH, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $N_3$, SH, $S(O)_nR^5$, $C(=O)R^5$, COOH, $COOR^5$, $CON(R^5)_2$, $C_1$ to $C_6$ alkyl optionally substituted with phenyl, methoxyphenyl, (dimethylamino)phenyl, $C(=O)R^5$, COOH, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring;

$R^5$ is $C_1$ to $C_6$ alkyl optionally substituted with phenyl, methoxyphenyl, (dimethylamino)phenyl, methoxy, ethoxy, benzyloxy, or with one or more F atoms, or $R^5$ is phenyl, methoxyphenyl, or (dimethylamino)phenyl; and n=0, 1, or 2.

Preferred among the compounds of the foregoing formula are those wherein R is a $C_2$ to $C_6$ (hydroxy)alkyl group optionally substituted with phenyl, $OR^5$, $N(R^5)C(=O)R^5$, $N(R^5)C(=O)OR^5$, or with one or more F atoms;

$R^1$, $R^2$, $R^3$ and $R^4$ are independently H, F, Cl, $CF_3$, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $C(=O)R^5$, $COOR^5$, $CON(R^5)_2$, $C_1$ to $C_6$ alkyl optionally substituted with phenyl, $C(=O)R^5$, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; and $R^5$ is $C_1$ to $C_6$ alkyl optionally substituted with phenyl, methoxyphenyl, methoxy, benzyloxy, or with one or more F atoms, or $R^5$ is phenyl or methoxyphenyl.

The deamination of the 1-(hydroxyalkyl)-3-aminoindazole can be accomplished by reaction according to general procedures known in the art as described, for example, in March (1992). Preferably the deamination is accomplished by treatment of the 1-(hydroxyalkyl)-3-aminoindazole with an organic nitrite in the presence of a hydride source and an organic solvent. Examples of suitable organic nitrites include, but are not limited to, tert-butyl nitrite, isobutyl nitrite, and isoamyl nitrite. The hydride source is preferably hypophosphorous acid or sodium hypophosphite. Most preferably the hydride source is hypophosphorous acid. The organic solvent may be an alcohol, such as methanol or ethanol, in which case the solvent can also function as a hydride source. Generally, the organic solvent is methanol.

Depending on the starting 2-(hydroxyalkyl)aminobenzonitrile, desired indazoles such as 1-(aminoalkyl)indazoles can be formed. As shown in the preferred embodiment and in the examples, the present invention essentially prevents the formation of unwanted isomers thus resulting in improved yields and a process that is less expensive. The process of the present invention can start with a racemic 2-(hydroxyalkyl)aminobenzonitrile, or can start with an (R)- or (S)-enantiomerically enriched 2-(hydroxyalkyl)aminobenzonitrile. Thus, the process of the present invention permits great flexibility in the starting 2-(hydroxyalkyl)aminobenzonitrile, which further permits great flexibility in forming various desired indazoles such 1-(aminoalkyl)indazoles. The indazoles which can be formed using the methods of the present invention are useful in, for instance, treating glaucoma and/or lowering or controlling elevated intraocular pressure.

The preferred process of the present invention uses a 2-alkylaminobenzonitrile in which the alkyl group is substituted by at least one OH group. The ability to have an OH group in such a reaction sequence is a great benefit and unexpected since those skilled in the art might expect that the OH group would not survive further processing. However, as shown in the examples, the method of the present invention allows formation of the desired indazole without the need for a protecting group on the hydroxy substituent. Thus, the present invention permits the formation of various desirable indazoles, which previous to the present process, were quite difficult to form.

With respect to the preferred reactants and the preferred reaction schemes, set forth below are preferred reaction schemes in the formation of a preferred 1-alkyl-3-aminoindazole which is then subsequently subjected to preferred reactions in the formation of the 1-alkylindazole. While the preferred components are set forth below, it is to be recognized that the present invention embraces other reactants, which in view of the present application, can easily be used by those skilled in the art.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

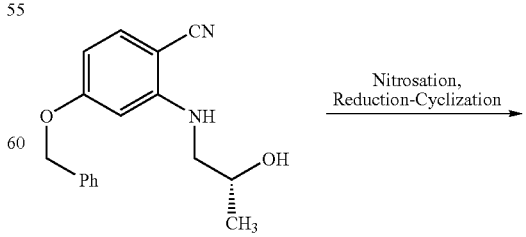

Scheme 1

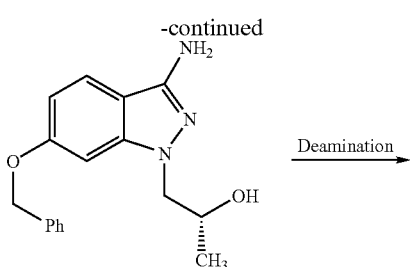

2

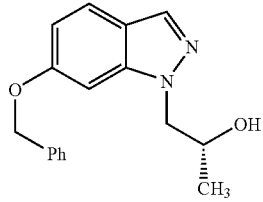

3

EXAMPLES

Preparation of (R)-6-Benzyloxy-1-(2-hydroxypropyl)-3-aminoindazole (2). Tert-butyl nitrite (759 mL, 6.38 mol) was added to a stirred solution of (R)-4-benzyloxy-2-(2-hydroxypropyl)aminobenzonitrile (1), prepared according to the methods described in WO 02/98861 A1 and WO 02/98862 A1 (1.20 kg, 4.25 mol) in 12 L of tetrahydrofuran under an atmosphere of nitrogen. After 1 h, the solution was cooled to 15° C., and 2.6 L of methanol was added followed by 10 L of saturated aqueous ammonium acetate solution. Zinc dust (1.1 kg, 17 mol) was added over 1.5 h, keeping the reaction temperature below 40° C. Ethyl acetate (10 L) was added, and the liquid phase was decanted from the solid residue and combined with that from one additional run on the same scale. The combined liquid phases were partitioned between ethyl acetate and brine. The organic solution was dried ($Na_2SO_4$), treated with decolorizing charcoal, filtered and concentrated in vacuo to afford 1976 g (78%) of 2.

Preparation of (R)-6-Benzyloxy-1-(2-hydroxypropyl)indazole (3). Hypophosphorous acid (3.45 L of a 50% (w/w) aqueous solution) was added to a stirred solution of 2 (1975 g, 6.65 mol) in 23.7 L of methanol under a nitrogen atmosphere. Isobutyl nitrite (1576 mL, 13.3 mol) was added in two portions, keeping the reaction temperature below 53° C. After 3 hours, a solution of $Na_2HPO_4$ (8.5 kg) in 70 L of water was added, and the mixture was extracted with ethyl acetate (30 L then 15 L). The combined organic extracts were washed with brine, dried ($Na_2SO_4$), treated with decolorizing charcoal, filtered and concentrated in vacuo. The product was purified by trituration with ethyl acetate-hexane followed by elution through silica using an acetone-hexane gradient, to give after concentration in vacuo, 1260 g (67%) of 3.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and structurally related may be substituted for the agents described herein to achieve similar results. All such substitutions and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

United States Patents and Published Applications
U.S. Pat. No. 3,133,081
U.S. Pat. No. 3,681,382
U.S. Pat. No. 3,725,431
Foreign Patents and Published Applications
DE 2,248,175
WO 98/30548
Books
March, Advanced Organic Chemistry, 4$^{th}$ edition, John Wiley and Sons, New York, pp. 721-723 (1992).
Other Publications
Kawakubo et al., Chem. Pharm. Bull. 35:2292 (1987).
Vivona et al., J. Heterocyclic Chem. 16:783 (1979).
Bouchet et al., Tetrahedron 36:3523 (1980).
Parnell, J. Chem. Soc. p. 2363 (1959).
Finch and Gschwend, J. Org. Chem. 36:1463 (1971).

What is claimed is:
1. A 1-alkyl-3-amino indazole of the formula

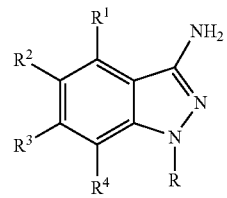

wherein R is a $C_2$ to $C_{12}$ (hydroxy)alkyl group optionally substituted with phenyl, methoxyphenyl, (dimethylamino)phenyl, $OR^5$, $OC(=O)R^5$, $OC(=O)OR^5$, $N(R^5)_2$, $N(R^5)C(=O)R^5$, $N(R^5)C(=O)OR^5$, or with one or more F atoms;

$R^1$, $R^2$, $R^3$ and $R^4$ are independently H, F, Cl, Br, $CF_3$, OH, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $N_3$, SH, $S(O)_n R^5$, $C(=O)R^5$, COOH, $COOR^5$, $CON(R^5)_2$, $C_1$ to $C_6$ alkyl optionally substituted with phenyl, methoxyphenyl, (dimethylamino)phenyl, $C(=O)R^5$, COOH, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; provided that at least one of $R^2$ and $R^4$ is H, OH, or $C_1$ to $C_6$ alkyl; and further provided that not more than one of $R^1$, $R^2$, $R^3$, and $R^4$ is $NO_2$, CN, or $S(O)_n R^5$ where n=1 or 2;

$R^5$ is $C_1$ to $C_6$ alkyl optionally substituted with phenyl, methoxyphenyl, (dimethylamino)phenyl, methoxy, ethoxy, benzyloxy, or with one or more F atoms, or $R^5$ is phenyl, methoxyphenyl, or (dimethylamino)phenyl; and $n=0$, 1, or 2.

2. The compound of claim 1, wherein

R is a $C_2$ to $C_6$ (hydroxy)alkyl group optionally substituted with phenyl, $OR^5$, $N(R^5)C(=O)R^5$, $N(R^5)C(=O)OR^5$, or with one or more F atoms;

$R^1$, $R^2$, $R^3$ and $R^4$ are independently H, F, Cl, $CF_3$, $OR^5$, $OC(=O)R^5$, $OC(=O)OR^5$, $N(R^5)_2$, $N(R^5)C(=O)R^5$, $N(R^5)C(=O)OR^5$, $NO_2$, CN, $C(=O)R^5$, $COOR^5$, $CON(R^5)_2$, $C_1$ to $C_6$ alkyl optionally substituted with phenyl, $C(=O)R^5$, $COOR^5$, $CON(R^5)_2$, CN, $OR^5$, $OC(=O)R^5$, $OC(=O)OR^5$, $N(R^5)_2$, $N(R^5)C(=O)R^5$, or $N(R^5)C(=O)OR^5$; or $R^1$ and $R^2$ as herein defined taken together form a ring, or $R^2$ and $R^3$ as herein defined taken together form a ring, or $R^3$ and $R^4$ as herein defined taken together form a ring; provided that at least one of $R^2$ and $R^4$ is H, OH, or $C_1$ to $C_6$ alkyl; and further provided that not more than one of $R^1$, $R^2$, $R^3$, and $R^4$ is $NO_2$, or CN; and $R^5$ is $C_1$ to $C_6$ alkyl optionally substituted with phenyl, methoxyphenyl, methoxy, benzyloxy, or with one or more F atoms, or $R^5$ is phenyl or methoxyphenyl.

\* \* \* \* \*